United States Patent [19]

Glascock et al.

[11] Patent Number: 5,585,565
[45] Date of Patent: Dec. 17, 1996

[54] METHOD FOR THE ULTRASONIC INSPECTION OF PIPE AND TUBING AND A TRANSDUCER ASSEMBLY FOR USE THEREWITH

[75] Inventors: James D. Glascock, Houston; Roy D. Felkner, Richmond; Gene M. Holmes, Houston, all of Tex.

[73] Assignee: Tuboscope Vetco International, Inc., Houston, Tex.

[21] Appl. No.: 389,569

[22] Filed: Feb. 16, 1995

Related U.S. Application Data

[63] Continuation of Ser. No. 88,039, Jul. 6, 1993, abandoned.

[51] Int. Cl.⁶ .................................................. G01N 29/04
[52] U.S. Cl. ...................... 73/644; 73/637; 73/622; 73/641; 73/638
[58] Field of Search ............................. 73/644, 622, 628, 73/637, 638, 641

[56] References Cited

U.S. PATENT DOCUMENTS

| | | | |
|---|---|---|---|
| 3,616,684 | 11/1971 | Nusbickel, Jr. | 73/641 |
| 3,631,714 | 1/1972 | Cressman et al. | 73/641 |
| 3,771,354 | 11/1973 | Miller | 73/641 |
| 3,777,552 | 12/1973 | Fletcher et al. | 73/622 |
| 3,777,554 | 12/1973 | Papay et al. | 73/641 |
| 3,798,961 | 3/1974 | Flambard et al. | 73/637 |
| 3,958,451 | 5/1976 | Richardson | 73/622 |
| 4,143,554 | 3/1979 | Nagg et al. | 73/641 |
| 5,007,291 | 4/1991 | Walters et al. | 73/622 |
| 5,079,952 | 1/1992 | Nakaso et al. | 73/641 |

*Primary Examiner*—Hezron E. Williams
*Assistant Examiner*—Helen C. Kwok
*Attorney, Agent, or Firm*—Finnegan, Henderson, Farabow, Garrett & Dunner, L.L.P.

[57] ABSTRACT

A transducer assembly and method for the ultrasonic inspection of tubing. An elastic membrane is used to form a reservoir of ultrasonic fluid coupled to ultrasonic transducers with the membrane conforming to the surface of the tubing being inspected. Guide wheels maintain the membrane out-of-contact with the tubing during relative rotational movement of the assembly and tubing during inspection. Water is introduced between the membrane and the tubing to provide ultrasonic coupling of the tubing to the transducers through the fluid of the reservoir.

4 Claims, 4 Drawing Sheets

METHOD FOR THE ULTRASONIC INSPECTION OF PIPE AND TUBING AND A TRANSDUCER ASSEMBLY FOR USE THEREWITH

This application is a continuation of application Ser. No. 08/088,039, filed Jul. 6, 1993, now abandoned.

BACKGROUND OF THE INVENTION

1. Field of the Invention

The invention relates to a method for the ultrasonic inspection of pipe and tubing to determine characteristics thereof, such as wall thickness or defects, and to a transducer assembly for use with this method.

2. Description of the Prior Art

Incident to the manufacture or use of tubular products, it is common practice to inspect the tubing for detection of variations in the wall thickness thereof and to detect the presence of surface and internal defects. For this purpose, it is known to use ultrasonic inspection techniques. With these techniques, it is customary to employ a transducer to impart high-frequency sound energy into the tubing to be tested. The high-frequency sound energy is transmitted through an ultrasonic fluid to the tubing and is reflected back from the tubing to the transducer. Monitoring of this back reflection of the sound energy is used to determine characteristics such as wall thickness and the presence of defects in the form of discontinuities in the tubing.

With inspection techniques of this type, relative rotational movement is imparted between the tubing being inspected and the transducer assembly used for the inspection. To achieve precise and reliable test results, it is necessary to maintain effective ultrasonic coupling between the transducers and the surface of the tubing during this relative rotational movement. This necessitates a transducer assembly having a surface coupled to the transducers that conforms to the contour of the surface of the tubing being inspected. To maintain this contact, it is desirable that the contacting surface of the transducer assembly be of a material that will deform into conformity with the tubing contour. For effective ultrasonic coupling, contact of the conforming material must be maintained while effecting relative rotational movement of the tubing surface and the conforming material of the transducer assembly. This results in rapid wear and destruction of this conforming surface of the transducer assembly and thus necessitates frequency removal and replacement. If the surface is attempted to be maintained in light contact to avoid wear and abrasion thereof, this results in ineffective ultrasonic coupling of the transducers and thus imprecise and unreliable test results.

SUMMARY OF THE INVENTION

It is accordingly a primary object of the present invention to provide an ultrasonic testing method for pipe and tubing and a transducer for use therewith wherein effective ultrasonic coupling may be maintained during relative rotational movement of a transducer assembly and tubing during ultrasonic testing, while avoiding wear and abrasion of the conforming surface portion of the transducer assembly.

A more specific object of the invention is to provide a method and assembly of this type wherein effective ultrasonic coupling may be provided between an ultrasonic transducer and tubing surface during relative rotational movement incident to inspection, while maintaining the conforming surface of the transducer assembly out of contact with the tubing surface.

The transducer assembly in accordance with the invention has an elongated housing with a plurality of ultrasonic transducers mounted on an upper surface of the housing and along a major axis thereof. A guide which may constitute a set of two wheels is mounted on each of two opposite ends of the housing. A plurality of ultrasonic transducers are mounted between the guides and on the housing. An elastic membrane of water-impervious, elastic material is provided in water-sealed connection at edge portions thereof to a lower surface of the housing. The edge portions of this membrane terminate on the lower surface of the housing at a location short of each guide. The elastic membrane forms a reservoir of ultrasonic fluid within the membrane, with this fluid being coupled to the plurality of transducers. Valves are provided for the selective and controlled introduction and removal of this ultrasonic fluid to and from the reservoir.

The ultrasonic fluid is preferably water.

The elongated transducer has an elongated, open interior portion on the upper surface thereof and the plurality of ultrasonic transducers are mounted within this open interior portion.

The reservoir provided by the membrane is in communication with this open interior portion of the elongated transducer housing.

The elastic membrane has an elongated flat bottom surface terminating at tapered opposed end portions adjacent each wheel.

In accordance with the method in the invention, the transducer assembly is employed by filling the reservoir with ultrasonic fluid and then compressing the fluid-filled membrane against an exterior surface of the tubing to be inspected. A quantity of the ultrasonic fluid is removed from the reservoir in an amount sufficient to permit the elastic membrane to conform to the contour of the exterior transverse surface of the tubing. Then inspection of the tubing is performed by introducing flowing ultrasonic liquid, preferably water, between the elastic membrane and adjacent surfaces of the tubing, while producing relative rotational movement between the transducer assembly and the tubing. During this operation, the elastic membrane and the plurality of ultrasonic transducer are ultrasonically coupled to the tubing by the flowing ultrasonic liquid and the ultrasonic fluid within the reservoir, while maintaining the elastic membrane out-of-contact with the tubing.

Preferably the water is introduced by spraying the water onto the tubing during the relative rotational movement between the transducer assembly and the tubing. This relative rotational movement is preferably produced by rotating the transducer assembly while moving the tubing linearly. It is also possible to maintain the transducer assembly stationary while simultaneously rotating and moving the tubing linearly.

DESCRIPTION OF THE PREFERRED EMBODIMENT

Figure 1:
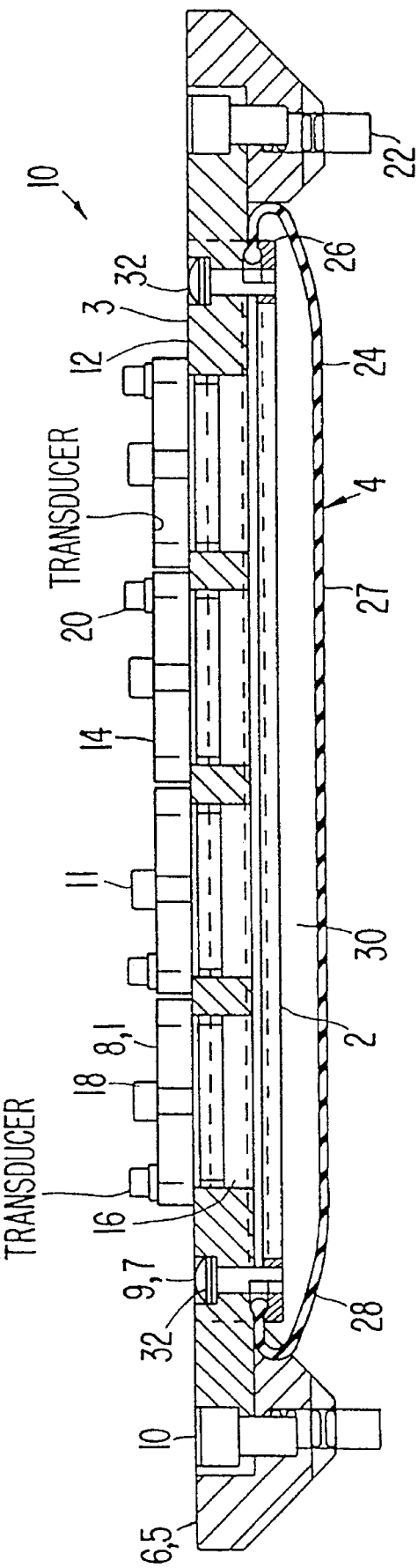
FIG. 1 is a sectional view of one embodiment of a transducer assembly in accordance with the invention taken along lines A—A of FIG. 2.
Figure 2:
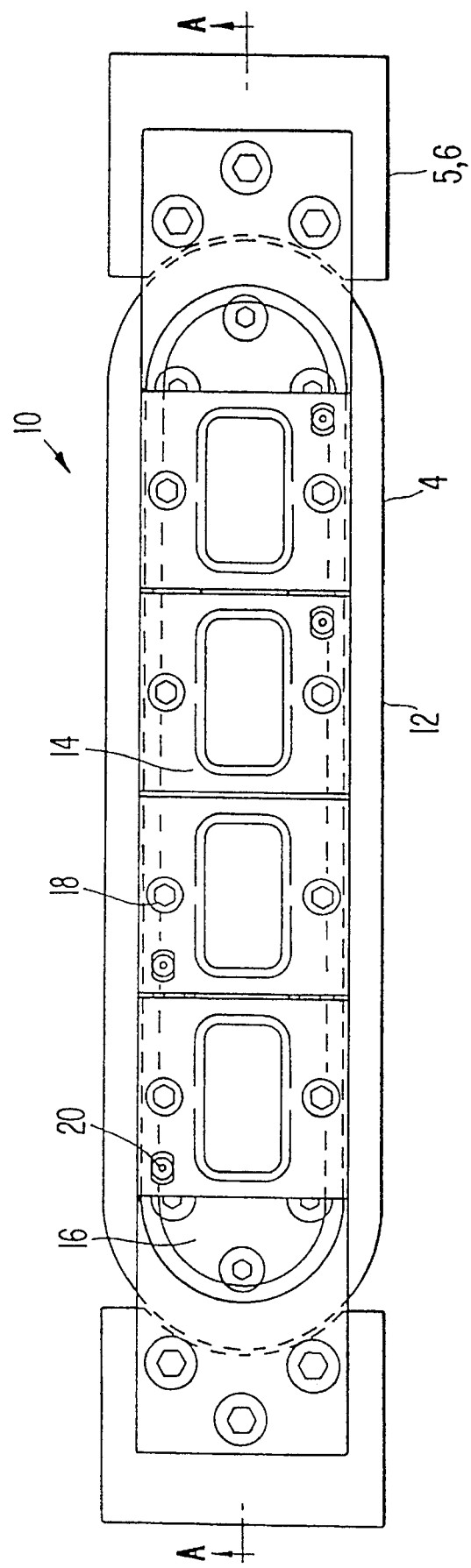
FIG. 2 is a plan view of the transducer assembly.

With reference to the drawings and for the present to FIGS. 1 and 2 thereof, there is shown a transducer assembly designated generally as 10 in accordance with one embodiment of the invention. The transducer assembly 10 has an elongated transducer housing 12. A plurality of transducers 14, four of which are shown in the embodiment of FIGS. 1 and 2, are mounted within an open area 16 of the transducer housing. The transducers 14 are secured within the open area 16 by bolts 18. Each transducer 14 has a terminal 20 for connection to a power source (not shown). A set of wheels 22 is journalled for rotation on each end of the transducer housing. An elastic membrane 24 of water-impervious, elastic material, such as polyurethane, is connected in water sealing engagement at edges 26 thereof to the transducer housing. The membrane 24 has a flat area 27 and tapered end portions 28. A reservoir 30 is provided by this membrane 24 between the membrane and the transducers mounted in the open area 16 of the transducer housing. Valves 32 are provided at each end of the reservoir to provide for the introduction and removal of water used as the ultrasonic coupling fluid with respect to the reservoir 30.

Figure 3:
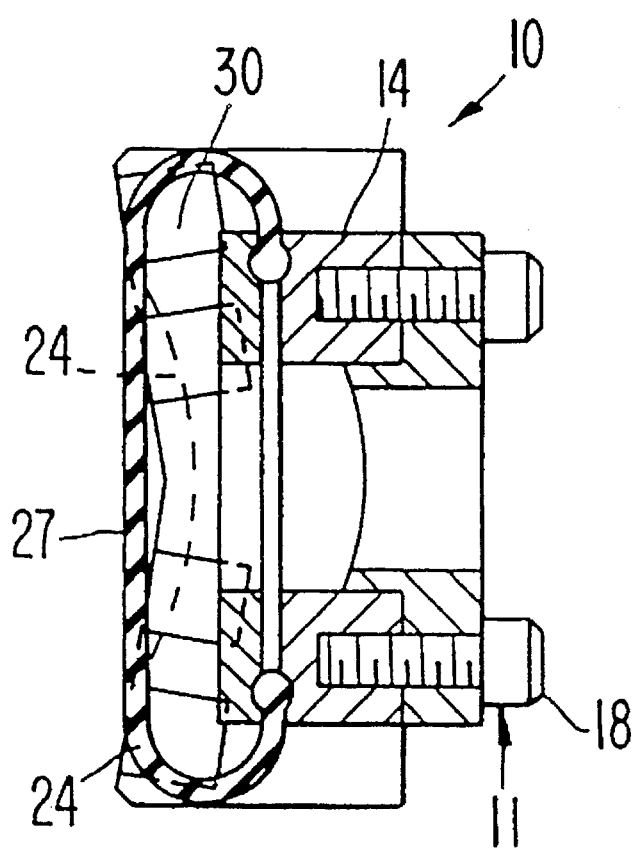
FIG. 3 is a detailed view in section of the transducer.
Figure 4:
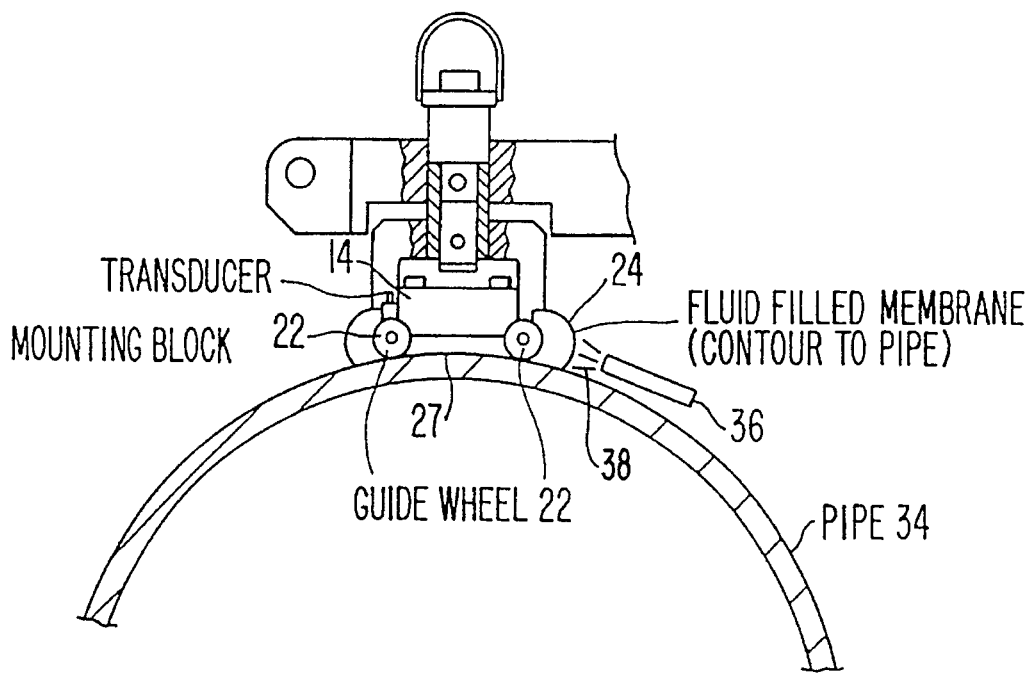
FIG. 4 is a perspective showing in side elevation of the ultrasonic inspection apparatus of the invention employing a transducer assembly in accordance with the embodiment of FIGS. 1, 2 and 3.
Figure 5:
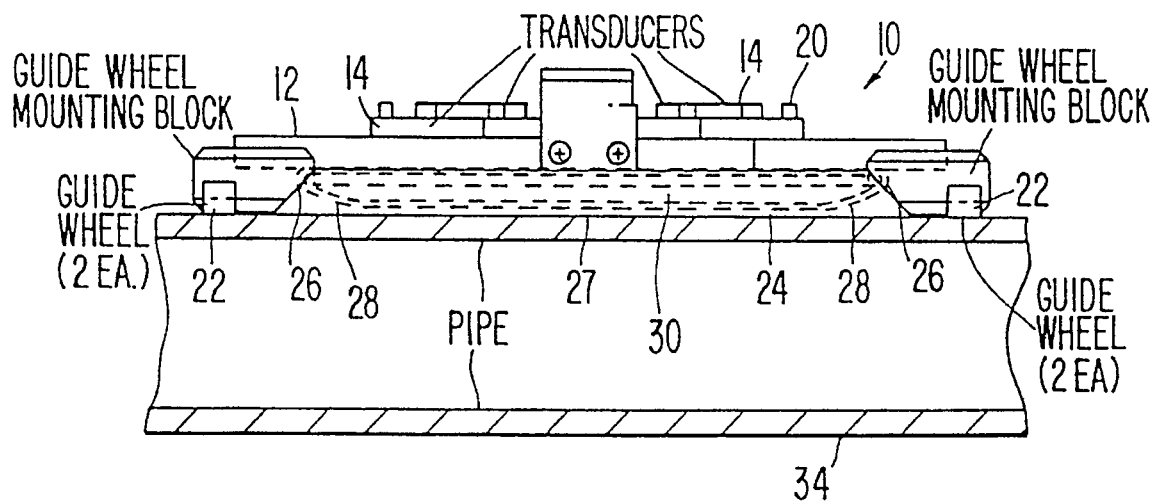
FIG. 5 is a perspective showing in front elevation of the apparatus of FIG. 4.

In accordance with the method of the invention, the reservoir 30 is filled with water through valves 32. Then the transducer assembly is placed adjacent the tubing to be inspected with the membrane 24 being compressed against the surface of the tubing. This causes distortion of the membrane to conform to the contour of the tubing, as shown by the dashed lines constituting the surface 27 of the membrane shown in FIG. 3. Then the water is removed through valves 32 until the membrane conforms to the surface of the tubing. FIGS. 4 and 5 show a tubing 34 to be inspected by the transducer assembly 10, with the surface 27 of the membrane 24 conforming to the contour of the tubing surface. During inspection, as shown in FIG. 4, the tubing is maintained out of contact with the surface 27 of the membrane during rotation thereof. This is achieved by water-spray nozzle 36 spraying water onto the rotating surface of the tubing to provide water between the surface 27 of the membrane 24 and the surface of the tubing 34. The membrane 24 is maintained out of contact by this flow of water 38 with the water maintaining the necessary ultrasonic coupling with the transducers of the assembly.

In this manner, effective ultrasonic coupling with the transducers is provided to achieve precise and reliable inspection, while protecting the surface 27 of the membrane 24 from contact and thus wear and abrasion caused by the tubing surface during inspection. The two sets of wheels 22 serve to guide the transducer assembly over the surface of the tubing to maintain accurate spacing relative to the tubing surface.

What is claimed:

1. A method for the ultrasonic inspection of tubing comprising, providing a transducer assembly including an elongated transducer housing having a plurality of ultrasonic transducers mounted on an upper surface and along a major axis of said housing, providing guides mounted on each of two opposed ends of said housing, with said plurality of ultrasonic transducers being mounted therebetween, providing an elongated elastic membrane of water-impervious, elastic material in water-tight sealed connection at edge portions thereof to a lower surface of said housing, with said edge portions of said membrane terminating on said lower surface of said housing at a location short of each said guides and with opposed width portions of said membrane extending beyond said housing, with said elastic membrane forming a reservoir of ultrasonic fluid within said membrane with said fluid being coupled To said plurality of transducers, providing means for selective and controlled introduction and removal of said ultrasonic fluid with respect to said reservoir, compressing said elastic membrane against an exterior surface of said tubing to be inspected, removing a quantity of said ultrasonic fluid from said reservoir sufficient to cause said elastic membrane to distort and conform to an arcuate contour of an exterior transverse surface of said tubing, introducing flowing additional ultrasonic liquid between said elastic membrane and an adjacent surface of said tubing, while producing relative rotational movement between said transducer assembly and said tubing to maintain said elastic membrane distorted and conforming to said arcuate contour of said exterior surface of said tubing and said plurality of ultrasonic transducers ultrasonically coupled to said tubing by said flowing ultrasonic liquid and said ultrasonic fluid within said reservoir, with said flowing ultrasonic liquid maintaining said elastic membrane out-of-contact with said tubing.

2. The method of claim 1, wherein said flowing ultrasonic liquid is water.

3. The method of claim 2, wherein said water is introduced by spraying said water onto said tubing during said relative rotational movement between said transducer assembly and said tubing.

4. The method of claim 2, wherein said relative rotational movement is produced by rotating said transducer assembly.

\* \* \* \* \*